(12) United States Patent
Cramer et al.

(10) Patent No.: US 10,011,827 B2
(45) Date of Patent: Jul. 3, 2018

(54) METHOD FOR ISOLATING NUCLEIC ACIDS FROM A FOOD SAMPLE

(71) Applicant: QIAGEN GmbH, Hilden (DE)

(72) Inventors: Janina Cramer, Hilden (DE); Sarah Fakih, Hilden (DE); Corinna Küppers, Hilden (DE); Holger Engel, Hilden (DE)

(73) Assignee: QIAGEN GmbH, Hilden (DE)

( * ) Notice: Subject to any disclaimer, the term of this patent is extended or adjusted under 35 U.S.C. 154(b) by 456 days.

(21) Appl. No.: 14/380,314

(22) PCT Filed: Feb. 28, 2013

(86) PCT No.: PCT/EP2013/054048
§ 371 (c)(1),
(2) Date: Aug. 21, 2014

(87) PCT Pub. No.: WO2013/127930
PCT Pub. Date: Sep. 6, 2013

(65) Prior Publication Data
US 2015/0056624 A1    Feb. 26, 2015

(30) Foreign Application Priority Data
Feb. 29, 2012    (EP) .................................... 12157537

(51) Int. Cl.
*C12N 15/10*    (2006.01)
*C12N 1/06*    (2006.01)
*C12Q 1/6806*    (2018.01)
*C12Q 1/689*    (2018.01)

(52) U.S. Cl.
CPC ............ *C12N 15/1003* (2013.01); *C12N 1/06* (2013.01); *C12N 15/1013* (2013.01); *C12Q 1/6806* (2013.01); *C12Q 1/689* (2013.01)

(58) Field of Classification Search
CPC .................................................. C12N 15/1003
USPC .............................................. 536/25.4, 25.41
See application file for complete search history.

(56) References Cited

U.S. PATENT DOCUMENTS

2009/0071830 A1* 3/2009 Vann ................. G01N 27/44782
204/543
2014/0024040 A1* 1/2014 Sabina ................. C12Q 1/6806
435/6.12

FOREIGN PATENT DOCUMENTS

| EP | 0 343 934 A2 | 11/1989 |
|---|---|---|
| EP | 1 256 627 A2 | 11/2002 |
| EP | 1 260 595 A2 | 11/2002 |
| EP | 1 559 478 A1 | 8/2005 |
| WO | 96/41811 A1 | 12/1996 |
| WO | 98/31461 A1 | 7/1998 |
| WO | 98/31840 A1 | 7/1998 |
| WO | 01/71732 A2 | 9/2001 |
| WO | 03/004150 A1 | 1/2003 |
| WO | 2004/003231 A2 | 1/2004 |
| WO | 2006/071770 A2 | 7/2006 |
| WO | 2010/108971 A1 | 9/2010 |

OTHER PUBLICATIONS

Ampe et al., "Polyphasic Study of the Spatial Distribution of Microorganisms in Mexican Pozol, a Fermented Maize Dough, Demonstrates the Need for Cultivation-Independent Methods to Investigate Traditional Fermentations," *Applied and Environmental Microbiology* 65(12):5464-5473 (Dec. 1999).
O'Grady et al., "Rapid real-time PCR detection of *Listeria monocytogenes* in enriched food samples based on the ssrA gene, a novel diagnostic target," *Food Microbiology* 25:75-84 (2008).
Sails et al., "A Real-Time PCR Assay for the Detection of *Campylobacter jejuni* in Foods after Enrichment Culture," *Applied and Environmental Microbiology* 69(3):1383-1390 (2003).
Uyttendaele et al., Detection of *Campylobacter jejuni* Added to Foods by Using a Combined Selective Enrichment and Nucleic Acid Sequence-Based Amplification (NASBA) *Applied and Environmental Microbiology* 61(4):1341-1347 (1995).

* cited by examiner

*Primary Examiner* — Jezia Riley
(74) *Attorney, Agent, or Firm* — Seed IP Law Group LLP

(57) ABSTRACT

The method for isolating nucleic acids from a food sample comprising the following steps: a) obtaining a food enrichment culture; b) transferring a portion of the food enrichment culture into a reaction vessel thereby providing a food enrichment sample and providing a water-immiscible phase in contact with the food enrichment culture; c) lysing the food enrichment sample to provide a lysed sample; d) isolating nucleic acids from the lysed sample. Food enrichment culture samples are known to contain high concentrations of organic and/or liposoluble inhibitors. By contacting the enrichment culture sample with a water-immiscible phase before the actual DNA extraction procedure starts, part of the lipophilic inhibitors is expected to cross the phase interface due to an enhanced solubility in the organic phase and thereby become depleted. The water-immiscible phase provided according to the invention interacts directly with the sample material throughout bacteria lysis and DNA extraction thereby optimizing the subsequent DNA purification processes due to the depletion of food-borne inhibitors. This method yields nucleic acids, in particular DNA that is of an improved quality and purity to be used in a subsequent PCR reaction to detect pathogen nucleic acids in the isolated nucleic acids.

23 Claims, 4 Drawing Sheets

METHOD FOR ISOLATING NUCLEIC ACIDS FROM A FOOD SAMPLE

FIELD OF THE INVENTION

The present invention pertains to a method for isolating nucleic acids, in particular DNA, from food samples. Said isolation method is particularly suitable for isolating DNA from a food enrichment culture that is suitable for food pathogen detection.

BACKGROUND OF THE INVENTION

During the past decades food safety concerns have steadily increased and are presently one of the most important challenges for food authorities. Growing emergence of food safety scares on one side and increased consumer preferences for minimally processed foods on the other side pose major challenges to food companies in controlling supply chains safety. In particular industrially processed foods represent a complex and challenging matrix for the detection of food-derived pathogens such as *Salmonella* and *Listeria* in routine food safety testing. With the requirement to detect down to one viable pathogen in 25 g of food, the majority of food safety testing laboratories still routinely apply classical, but extremely time-consuming, microbiological culturing methods to verify bacterial growth. For example *salmonella*, which is a major cause for food-borne bacterial infections throughout the world, requires five days for a classical microbiological confirmation. A classical microbiological *salmonella* confirmation comprises several steps. First, a potentially *salmonella*-contaminated food sample is incubated in an initial 18 hour overnight pre-enrichment culture, followed by an additional 24 hour selective enrichment phase. The culture is subsequently streaked on a selective nutrient agar (24 hour incubation) and characteristic colonies are further cultivated for final bacteria detection (24 hour incubation). Confirmation is carried out on the fifth day either biochemically or serologically.

Such time consuming methods can not be integrated in the regular flow of the food supply chain. A clear gap exists between microbiological product approval processes in the range of several days to weeks and food factory realities dealing with raw and perishable materials, creating an urgent need for short, flexible and easy-to-use testing methods. In this context, a workflow consisting of efficient pathogen nucleic acid extraction in combination with highly selective detection such as by real-time PCR has gained considerable importance in routine pathogen testing for food production and safety chains.

In food diagnostics methods that are based on molecular biological detection methods the pathogen detection workflow also starts from a food enrichment culture, in which the potentially contaminated food type is mixed with an enrichment medium and incubated at an elevated temperature for a certain amount of time. Under these conditions the number of contaminating pathogens is increased above an analytically detectable number. The preparation of an enrichment culture is necessary to process only viable pathogens in the subsequent extraction and detection steps and to guarantee a safely detectable pathogen concentration within the highly inhibitory food matrix. To prepare a food enrichment culture for the subsequent nucleic acid isolation usually an amount of potentially contaminated food (usually 25 g) is mixed with a defined volume of an enrichment medium. This food/medium mixture is incubated at raised temperature for a specific time (e.g. 18 h for *Salmonella*) to grow and enrich the contaminating pathogen above an analytically detectable level. The resulting enrichment culture comprises a high concentration of the food-borne pathogens but at the same time a dense matrix of food-derived inhibitors. Thus, the food sample is often highly inhibitory to the subsequent isolation and detection process. This is, because food samples differ in their nature and regularly comprise a multitude of different food-derived inhibitors in a high concentration. Therefore, even after enrichment, the isolation of a sufficient amount of nucleic acids with acceptable purity that allows to perform the subsequent pathogen detection steps is challenging.

Thus, the successful detection of food-borne pathogens in a food sample strongly depends on efficient protocols for the extraction and purification of pathogen nucleic acids such as bacteria DNA from complex food matrices. Here, the efficient depletion of most of the food-borne inhibitors is a crucial prerequisite for the reliable isolation of nucleic acids that can be subsequently used for molecular biological pathogen detection e.g. using a PCR based detection method.

To provide a nucleic acid method that is suitable for isolating pathogen nucleic acids from various food samples is particularly challenging, if a simple, rapid protocol is supposed to be provided that is also suitable for automation. Automation is a key requirement of the food industry. For highly standardized and safe routine food safety testing, the industry strongly requires a complete workflow line, applying a minimum of manual interactions from sample preparation to pathogen detection. A fully automated pathogen detection workflow is required to offer maximal process safety and rapid high throughput protocols while allowing for flexible sample volume and sample type. Furthermore, as discussed above with the emergence of a globalized market, food industry is in demand for reliable, accurate, and stable pathogen detection systems.

Thus, it is the object of the present invention to provide a method for isolating nucleic acids from a food sample that overcomes at least one of the prior art drawbacks. In particular, it is an object to provide an improved nucleic acid isolation protocol that allows to isolate pathogen derived nucleic acids, in particular DNA, from various food samples.

SUMMARY OF THE INVENTION

The present invention is based on the finding that the isolation of pathogen nucleic acids, in particular pathogen DNA, from food samples can be considerably improved, if the food enrichment sample is contacted with a water-immiscible composition prior to isolating the nucleic acids. Preferably, the water-immiscible composition forms an organic phase on the food enrichment sample. Contacting the food enrichment sample with a water-immiscible phase, which can e.g. be provided by a layer of mineral oil, surprisingly has the effect that the nucleic acid isolation is significantly improved. Without being bound by theory, it is assumed that the water-immiscible organic phase that is provided in contact with the food enrichment sample has the effect that organic and/or liposoluble inhibitors that originate from the food sample are depleted from the unprocessed food enrichment sample during the extraction of the nucleic acids. The water-immiscible composition basically works as an inhibitor removal reagent thereby optimising inhibitor depletion. Thereby, a method is provided for isolating nucleic acids from food enrichment cultures which yield pathogen nucleic acids such as bacteria DNA of higher quality and/or purity. As is shown in the examples, the nucleic acid isolation method according to the present invention provides improved results over methods wherein no water-immiscible phase is provided in contact with the food enrichment sample. Furthermore, it is quick and suitable for automation.

According to a first aspect of the present invention, a method for isolating nucleic acids, in particular pathogen DNA, from a food sample is provided, which comprises the following steps:
a) obtaining a food enrichment culture;
b) transferring a portion of the food enrichment culture into a reaction vessel thereby providing a food enrichment sample and contacting the food enrichment sample with a water-immiscible composition;
c) lysing the food enrichment sample to provide a lysed sample, preferably by performing a thermal treatment;
d) isolating nucleic acids from the lysed sample.

According to a second aspect, a method for determining the presence or absence of a pathogen in a food sample is provided, said method comprising performing the method according to the first aspect of the present invention and analyzing the isolated nucleic acids.

According to a third aspect, the present invention pertains to the use of a water-immiscible composition for removing inhibitors from a food enrichment sample. The present invention provides a water-immiscible composition such as mineral oil as an efficient purification reagent for the depletion of organic and/or lipophilic inhibitors from unprocessed food enrichment culture samples. As is shown in the examples, contacting the food enrichment sample with a water-immiscible phase is favourable during the extraction of nucleic acids such as DNA from food-borne pathogens, in particular bacteria.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

Figure 1A:
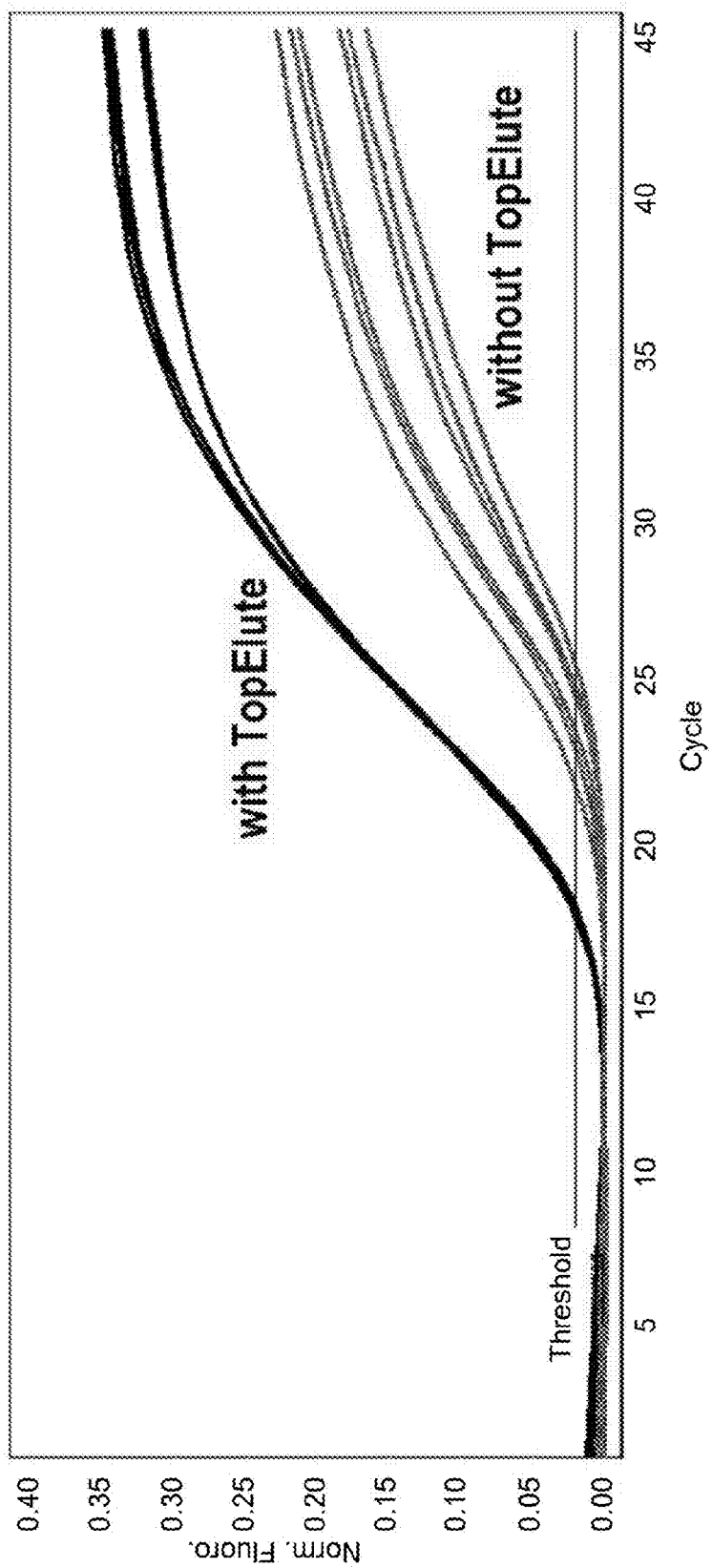
FIG. 1: A) Smoked salmon and B) ground beef was inoculated with ~20 cfu *salmonella* and incubated in Buffered Peptone Water for 18 h at 37° C. Samples of the enrichment culture were directly processed according to example 1/Protocol (1) (black), applying mineral oil ("TopElute"), and the analogous protocol lacking TopElute (grey). Comparison of protocol performances with both food types shows that DNA yield as well as scattering of the extraction replicates and end fluorescences is significantly better if the TopElute is applied.

According to a first aspect of the present invention, a method for isolating nucleic acids, in particular pathogen DNA, from a food sample is provided, which comprises the following steps:
a) obtaining a food enrichment culture;
b) transferring a portion of the food enrichment culture into a reaction vessel thereby providing a food enrichment sample and providing a water-immiscible phase in contact with the food enrichment sample e.g. by contacting the food enrichment sample with a water-immiscible composition;
c) lysing the food enrichment sample to provide a lysed sample, preferably by performing a thermal treatment;
d) isolating nucleic acids from the lysed sample.

The method according to the first aspect of the present invention will be subsequently explained by describing each individual step a) to d) in detail. Furthermore, preferred embodiments of the present invention are described.

In step a), a food enrichment culture is provided. A food enrichment culture can be prepared by contacting a food sample with a culture medium. Any food sample can be processed with the method according to the present invention, including but not limited to raw food, processed food, meat, fish, poultry, vegetables, eggs, dairy products, such as cheese, milk, yoghurt, cream, bakery products, chocolate, peanut butter, beverages and the like. The method according to the present invention is in particular suitable to process difficult food samples such as very fatty food products and/or food samples that comprise a high concentration of food-derived inhibitors such as in particular organic and/or liposoluble inhibitors. Advantageously, when using the method according to the present invention it is not necessary to distinguish between specific food types, e.g. comprising a high or a low amount of inhibitors, because diverse food samples can be efficiently processed with the method according to the present invention. When contacting the food sample to be analysed with the culture medium, the resulting mixture can be homogenized, e.g. using a lab pedal blender. The resulting mixture is usually incubated at a specific temperature in order to allow the growth of the suspected pathogens, e.g. specific bacteria. Generally, the food enrichment cultures will be provided according to the methods that are specified by the food regulatory authorities of the individual countries. These may require the use of specific culture media and/or culturing conditions for specific food samples and/or pathogens to be detected. E.g. in Germany, food enrichment cultures are usually prepared according to § 64 LFGB. The enrichment can be performed un-selectively or selectively. When performing a selective enrichment of a specific target pathogen, usually a pre-enrichment culture is prepared in an un-selective culture medium that allows to grow the target pathogen of interest and afterwards, a selective enrichment is performed using a bacteria-specific enrichment medium which supports the growth of the target pathogen of interest but does not allow or at least impedes growth of non-target pathogens or non-target microorganisms. Suitable culture media for classical pathogens such as *Salmonella* and *Listeria* are known in the prior art and thus, need no specific description herein. However, it is a specific advantage of the present invention that it is not necessary to perform a selective enrichment prior to isolating the nucleic acids, in particular pathogen DNA, from the food enrichment culture. As is shown in the examples, the method according to the present invention enables the reliable isolation of pathogen nucleic acids such as pathogen DNA from un-selective food enrichment cultures. E.g. a single un-selective enrichment step in a *Salmonella*-recommended medium such as Buffered Peptone Water has shown to already provide a suitable starting material for a stable DNA extraction. For the ease of simplicity it is thus preferred that the food enrichment culture is provided by contacting the food sample with an un-selective enrichment medium which, however, is suitable for growing the target pathogen(s) of interest and incubation under conditions suitable to provide the food enrichment culture.

Following the respective standards for culturing a food sample, performing step a) provides a food enrichment culture that can be further processed according to the present invention to isolate pathogen derived nucleic acids such as in particular bacteria DNA from the food enrichment culture.

In step b), a portion of the food enrichment culture is transferred into a reaction vessel. For this purpose, usually an appropriate aliquot of the food enrichment culture such as for example 100 µl to 1500 µl, 150 µl to 1000 µl, 200 µl to 750 µl or preferably 250 µl to 500 µl is transferred into the reaction vessel. The reaction vessel can have any form or size and said term also includes devices comprising multiple reaction wells as reaction vessels. If desired, intermediate preparation steps of the food enrichment culture such as e.g. a centrifugation step can be performed. However, such preparation steps are not mandatory because the nucleic acid isolation method according to the present invention allows the direct processing of the crude, i.e. unprocessed food enrichment culture. The food enrichment sample is contacted with a water-immiscible composition such as e.g. mineral oil, thereby providing a water-immiscible phase, in particular a layer, in contact with the food enrichment sample. This is an essential step of the method according to the present invention.

As discussed above, providing a water-immiscible phase in contact with the food enrichment sample improves the nucleic acid isolation results. The water-immiscible phase may be provided on top of the food enrichment sample or may be provided below the food enrichment sample. Preferably, it is provided on top of the food enrichment sample. Without being bound by theory, it is assumed that by bringing the food enrichment sample in contact with a water-immiscible phase, inhibitors such as in particular food-derived inhibitors are removed from the food enrichment sample. Such inhibitors can disturb the nucleic acid isolation process, respectively represent inhibitors in the isolated nucleic acids that can disturb downstream analysis or detection methods if they are not effectively removed. As the nucleic acid isolation protocol is supposed to be simple and rapid, such inhibitors pose a specific problem. Providing the water-immiscible phase in contact with the food enrichment sample apparently has the surprising effect, that in particular organic and/or liposoluble inhibitory components are extracted from the food enrichment sample into the water-immiscible phase. Thereby, the food enrichment sample is depleted from respective inhibitors and accordingly, the nucleic acid isolation can be improved. Respective inhibitors may originate from the food sample and are accordingly food-borne or may also derive from the pathogens comprised in the food sample, respectively the food enrichment sample. For a maximal effect the water-immiscible composition which provides the water-immiscible phase is brought into direct contact with the unprocessed food enrichment sample containing viable and intact bacteria. In the resulting two-component system lipophilic inhibitors are believed to cross the phase interface potentially according to the mechanism of a small scale phase extraction. This step represents an important pre-cleaning step in which inhibitors are reduced already before the sample is chemically modified and before the pathogens are lysed.

The water-immiscible phase can be provided by first transferring the food enrichment sample into the reaction vessel and then overlaying the food enrichment sample with the water-immiscible phase e.g. in form of a closed layer. Alternatively, the water-immiscible composition can be provided first and the food enrichment sample can be pipetted on top of the water-immiscible layer or can be pipette e.g. through said water-immiscible phase into the reaction vessel. In all cases, a water-immiscible phase is provided that is in contact with the food enrichment sample. Preferably, after contacting the food enrichment sample with the water-immiscible composition, a water immiscible phase is formed on top of the food enrichment sample.

Several compounds and mixtures of compounds are suitable for providing the water-immiscible phase and accordingly, can be used as water-immiscible composition. The water-immiscible phase preferably is an organic phase. It is lipophilic. Principally all liquids or mixtures of liquids, which substantially are not miscible with water and which on the addition of water built a phase with a pronounced phase border, are suitable as water-immiscible composition that can be used to provide the water-immiscible phase. The water-immiscible composition is preferably also immiscible with alcohol or other hydrophilic or aqueous fluids. Preferably, the water-immiscible phase is provided by at least one substituted or non-substituted, branched or unbranched hydrocarbon. Furthermore, the water-immiscible phase may comprise a cyclic, saturated or unsaturated hydrocarbon (like e.g. cyclo hexane) or an aromatic hydrocarbon (like e.g. benzene or toluene etc.), wherein such hydrocarbons are not miscible with water. According to one embodiment, the hydrocarbons used according to the invention to provide the water-immiscible phase may bear as substituents e.g. one or more halogen atom(s), nitro group(s) and/or amino group(s). In preferred embodiments of the invention, the water-immiscible layer comprises hydrocarbons, preferably saturated hydrocarbons, or consists thereof. Suitable hydrocarbons are branched or unbranched, substituted or non-substituted, acyclic or cyclic hydrocarbons with 5, 6, 7, 8, 9, 10, 11, 12, 13, 14, 15, 16, 17, 18, 19 or 20 carbon atoms. E.g. branched or unbranched substituted acyclic or cyclic hydrocarbons with 6, 7, 8, 9, 10, 11, 12, 13, 14, 15 or 16 carbon atoms can be used. Non-substituted, acyclic branched or unbranched hydrocarbons with 8, 9, 10, 11, 12 or 13 carbon atoms can be used, among which n-octane, n-nonane, n-decane and/or n-dodecane or mineral oils are very especially preferred. N-Octane, n-nonane, n-decane and/or n-dodecane as well as mixtures thereof are even further preferred. The term "mineral oil" in particular refers to the liquid destillation products derived from mineral raw materials like e.g. petroleum, brown and black coals, wood or peat, which substantially consist of mixtures of long-chained, aliphatic and saturated hydrocarbons. Destillation products or mixtures of hydrocarbons, respectively, like e.g. white oil and/or other paraffin oils, which mainly contain long-chained alkanes with preferably 13 to 20, especially preferably 14 to 16 carbon atoms, are especially preferred. Other examples include liquid waxes. The water-immiscible phase which preferably forms a layer on the food enrichment sample may also comprise silicone oil or consist thereof. Silicone oils are suitable, because they are inert against other substrates to a high degree and show high spreadability, which accompanies the formation of certain properties, e.g. the hydrophobicity. Especially, suitable silicone oils are synthesis oils based on semiorganic polymers and copolymers of silicon-oxygen units with organic side chains. Polymers or copolymers of unbranched chains made up of alternating silicon and oxygen atoms are preferred. All afore mentioned compounds may be used in form of mixtures (e.g. a hydrocarbon mixture like mineral oil) to provide the water-immiscible phase which can be used to overlay the food enrichment sample.

The water-immiscible composition is added in an amount suitable to provide a closed water-immiscible phase which preferably is provided on top of the food enrichment sample. Providing a closed layer ensures a close interaction between the water-immiscible phase and the food enrichment sample what is deemed advantageous for achieving a good purifying effect. The amount of water-immiscible composition that has to be added to achieve a respective full coverage of the food enrichment sample in particular depends on the design and dimension of the reaction vessel that is used to process the food enrichment sample. Preferably, the food enrichment sample is contained in a reaction vessel that provides a large surface area as thereby, the interaction between the water-immiscible phase and the food enrichment sample is improved. This is advantageous for the depletion effect. Furthermore, the water-immiscible phase is preferably thicker if the food enrichment sample comprises a high concentration of food-borne inhibitors. Suitable amounts can be determined by the skilled person using the information and guidance provided herein.

After providing the water-immiscible phase in contact with the food enrichment sample, preferably on top of the food enrichment sample, said sample is ready for lysis in step c). This lysis step serves the purpose to lyse pathogens such as in particular bacteria that are potentially comprised in the food enrichment sample. According to a preferred embodiment of the method of the present invention, a thermal treatment is performed in step c) to promote the lysis of the food enrichment sample. Step c) is an important step which is according to the preferred teachings of the present invention highly efficient and simple. Preferably, a thermal treatment is performed to lyse the food enrichment sample and in particular to lyse the pathogens comprised therein, wherein said thermal treatment comprises heating the food enrichment sample that is contact with, preferably is overlayed with the water-immiscible phase for 2 to 20 minutes, preferably 3 to 15 minutes, more preferred 3 to 10 minutes, most preferred 3 to 5 minutes at least at 80° C., preferably at least at 85° C., more preferred at least at 89° C. For example the food enrichment sample can be heated at approximately 89° C. to 100° C. for 5 minutes. As it is shown by the examples, this short heating step already results in a very efficient lysis of bacteria, that are potentially comprised in the food enrichment sample. This heating step can thus substitute time consuming and costly enzymatic lysis steps. Of course also longer incubation times and/or higher temperatures can be used for thermal lysis, however, they are not necessary as is shown in the examples. This advantageously saves time and costs. Performing the lysis of the food enrichment sample by a thermal treatment efficiently contributes to the short protocol times that are achieved with the method according to the present invention. Furthermore, it makes the method according to the present invention well suitable for automation. Unprocessed food enrichment culture samples can be directly loaded onto the robotic instrument and are then heat treated within the system for lysis. The lysis and isolation methods described herein work with gram-negative (e.g. *Salmonella*) and gram-positives (e.g. *listeria monocytogenes*) bacteria.

As is shown by the examples, the nucleic acid isolation is efficient using the method according to the present invention, if the food enrichment sample is subjected only to a thermal lysis step. As a thermal treatment represents a chemistry/enzyme-independent lysis procedure, it is equally applicable for both bacteria types. It is not mandatory to add or use further lysis components or lytic agents in order to lyse the sample and in particular to lyse the potentially comprised pathogens. However, it is also within the scope of the present invention and even preferred for certain applications/pathogens, to assist the lysis of the sample by adding further reagents. Thus, according to one embodiment, the present method comprises the addition of one or more reagents that support the lysis of the food enrichment sample prior to or during step c).

Preferably, the lysis of the food enrichment sample is carried out in the presence of a chaotropic agent. Of course, also more than one chaotropic agent can be used. Thus, according to one embodiment, a chaotropic agent and optionally further additives, is added to the food enrichment sample prior to performing a thermal treatment in step c). Thereby, the chaotropic agent is present during the thermal lysis and can support the lysis procedure. This is particularly beneficial if the target pathogen is a gram-positive bacteria as this type of bacteria is more difficult to lyse. Of course, said protocol works also efficient with gram-negative bacteria. Any chaotropic agent can be used that causes disorder in a protein or nucleic acid by, for example, but not limited to altering the secondary, tertiary or quaternary structure of a protein or a nucleic acid. Preferably, a chaotropic salt is used. The chaotropic salt preferably comprises guanidinium, thiocyanate, isothiocyanate, perchlorate, trichloroacetate and/or trifluoroacetate as chaotropic ion. Preferably, the chaotropic agent is selected from the group consisting of guanidinium hydrochloride, guanidinium thiocyanate, guanidinium isothiocyanate, sodium thiocyanate, sodium iodide, sodium perchlorate, sodium trichloroacetate, sodium trifluoroacetate and urea. Also a mixture of chaotropic agents can be used. Preferably, guanidinium hydrochloride, guanidinium thiocyanate or guanidinium isothiocyanate is used as chaotropic agent for lysis. Preferably, the chaotropic agent is contained in a solution such as a lysis buffer that is added to the food enrichment sample. The lysis solution, such as a lysis buffer or lysis supporting buffer, may comprise the chaoptropic agent, which preferably is a chaotropic salt as mentioned above, in a concentration that lies in a range selected from about 0.1M up to the saturation limit, about 0.2M to 6M, about 0.5M to 4M or about 1M to 3M. This embodiment has the advantage that it not only supports the lysis of the sample but also contributes to directly set up the conditions for the nucleic acid isolation step d). Thus, the lysis solution may also function as a binding solution and vice versa. Details of this embodiment will be described subsequently.

Furthermore, to support the lysis of the sample also one or more further additives can be added to the food enrichment sample. Examples of suitable reagents include but are not limited to detergents, alcohols and buffers.

As detergent, an ionic, non-ionic or zwitterionic detergent can be used. According to one embodiment, a non-ionic detergent is added for lysis. Preferably, a polyoxyethylene fatty alcohol ether is used as non-ionic detergent. The term "fatty alcohol" in particular refers to alcohols having a chain length of from 6 to 22 carbon atoms, preferably 8 to 20 carbon atoms, preferentially 10 to 18 carbon atoms, particularly preferably 12 to 18 carbon atoms. Preference is in particular given to alcohols having 12, 14, 16 or 18 carbon atoms. Although the fatty alcohols may be mono- or poly-unsaturated, they are preferably saturated fatty alcohols. The term "polyoxyethylene" in particular refers to an HO—(CH2CH2O)n unit, with n being preferably an integer from 2 to 150, further preferably from 4 to 120, still further preferably from 8 to 80. Preferred examples of suitable polyoxyethylene fatty alcohol ethers are polyethoxylated lauryl, cetyl, oleyl, or stearyl alcohols which may be used alone or as mixture. According to a preferred embodiment of the invention, the at least one polyoxyethylene fatty alcohol ether comprises a fatty alcohol component having from 6 to 22 carbon atoms and a polyoxyethylene component having from 2 to 150 (CH2CH2O) units. Preferably, the polyoxyethylene fatty alcohol ether is selected from the group consisting of polyoxyethylene lauryl ether, polyoxyethylene cetyl ether, polyoxyethylene stearyl ether and/or polyoxyethylene cetyl ether. Other non-ionic detergents that can be used during lysis include but are not limited to alkylglucosides and polyoxyethylene alkyl phenyl ethers. As alkylglucoside, preferably a non-ionic detergent from the group of the polysorbates, preferably polysorbate 20, polysorbate 40 or polysorbate 80, more preferred polysorbate 20 is used. Preferred examples of polyoxyethylene alkyl phenyl ethers include Triton X-100 and Nonidet P-40. Also mixtures of different detergents can be added. The respective detergents may also be included in the lysis solution comprising the chaotropic agent (see above).

Further additives may be added to support the lysis of the food enrichment sample and/or to protect the released nucleic acids from degradation. Respective compounds that may protect released nucleic acids are well known in the prior art and thus, do not need a detailed description here. Respective compounds may be added separately to the food enrichment sample or may be included in the lysis solution comprising the chaotropic agent.

The water-immiscible phase may be still in contact with the food enrichment sample in lysis step c), which preferably is a thermal lysis step. As discussed above, depending on the embodiment used this thermal lysis procedure is either entirely based on a heat treatment and/or is chemically supported e.g. by the addition of a chaotropic agent and optionally further additives. In both embodiments the water-immiscible phase is preferably present during the entire lysis procedure, thereby being capable of further depleting inhibitors that are released during the lysis procedure, in particular for depleting inhibitors that are released due to the lysis of the comprised pathogens. Preferably, the water-immiscible phase is provided on top of the sample during lysis step c).

According to one embodiment, also an alcohol is added prior to the lysis of the food enrichment sample. The alcohol is preferably a short chained branched or unbranched alcohol with 1 to 5 carbon atoms. Preferably, it is selected from methanol, ethanol, propanol, isopropanol and butanol. Particularly suitable are ethanol and isopropanol. Adding an alcohol in addition to the chaotropic agent prior to performing the thermal lysis has several advantages. In particular, the alcohol can assist the nucleic acid isolation in step d) as will be described below. If the food enrichment sample is overlayed with a water-immiscible phase, evaporation of the alcohol during thermal lysis is reduced or prevented.

As described above, the one or more reagents that can be added prior to performing the lysis in step c) may conveniently be comprised in a lysis solution. The respective lysis solution preferably comprises at least one chaotropic agent, preferably a chaotropic salt, at least one detergent and preferably at least one alcohol as is described above if the lysis solution also serves the purpose to establish the binding conditions. Furthermore, it may comprise a buffering compound. Said lysis solution may be added prior to providing the water-immiscible phase and/or the food enrichment sample or afterwards. Usually, it is well possible to pipet an aqueous solution such as a lysis buffer through the water-immiscible layer if the water-immiscible phase is provided on top of the food enrichment sample.

If the nucleic acid is isolated in step d) by binding the nucleic acid to a nucleic acid binding solid phase, binding conditions must be set up that allow to bind the nucleic acid to the used nucleic acid binding solid phase. The chaotropic agent and the one or more optional additives that can be added prior to lysis are (if added) comprised in the lysed sample and accordingly, contribute to the binding conditions. Accordingly, they can promote the binding of the nucleic acids to the nucleic acid binding solid phase if such nucleic acid binding solid phase is used in step d) what is preferred as is described below. Accordingly, the embodiment wherein a chaotropic agent and preferably also an alcohol is added prior to performing the thermal lysis has additionally the advantage that the addition of a separate binding solution after the thermal lysis step becomes obsolete as the binding conditions are already established.

According to one embodiment, the lysis of the food enrichment sample does not involve the use of a proteolytic enzyme such as a protease. This embodiment has the advantage that the lysis is very cost-efficient and quick because longer incubation times are obsolete that are otherwise needed to enable the enzymatic sample digestion.

After lysis in step c), which preferably is a thermal lysis as described above, the nucleic acids are isolated in step d) from the lysed sample. Here, basically any nucleic acid isolation method can be used that is suitable for isolating nucleic acids, in particular DNA, from a lysed sample. Suitable nucleic acid isolation methods are known in the prior art and include but are not limited to extraction, solid-phase extraction, silica-based purification methods, nucleic acid isolation procedures using chaotropic agents and/or at least one alcohol and a nucleic acid binding solid phase, magnetic particle-based purification, phenol-chloroform extraction, chromatography, anion-exchange chromatography (using anion-exchange surfaces), filtration, precipitation, and combinations thereof. Such methods are known in the prior art and thus, do not need a detailed description here. Preferred embodiments which enable a simple and rapid DNA isolation that is also suitable for automation are described below. Preferably, the nucleic acids are isolated in step d) using an automated system. As discussed above, using an automated system meets the needs of the food industry for quick and simple sample processing. Furthermore, automated systems allow to process large sample quantities. The samples can be processed batchwise.

Preferably, the nucleic acids are isolated by binding the nucleic acids to a nucleic acid binding solid phase. As nucleic acid binding solid phase, any material that is capable of binding nucleic acids present in the lysed sample can be used. A variety of materials are well-known that are capable of binding nucleic acids under suitable conditions. Exemplary solid phases that can be used in conjunction with the present invention include, but are not limited to, compounds comprising silica, including but not limited to, silica particles, silicon dioxide, siliceous materials, minerals, zeolithes, diatomaceous earth, glass, alkylsilica, aluminum silicate, and borosilicate; nitrocellulose; diazotized paper; hydroxyapatite (also referred to as hydroxyl apatite); nylon; metal oxides; zirconia; alumina; polymeric supports, diethylaminoethyl- and triethylaminoethyl-derivatized supports, hydrophobic chromatography resins (such as phenyl- or octyl Sepharose) and the like. The nucleic acid binding solid phase may derivatized with functional groups or may not be derivatized with functional groups. According to one embodiment, the solid phase does not comprise cationic groups. The term solid phase is not intended to imply any limitation regarding its form or design. Thus, the term solid phase encompasses appropriate materials that are porous or non-porous; permeable or impermeable; including but not limited to membranes, filters, sheets, particles, magnetic particles, beads, gels, powders, fibers, and the like. According to one embodiment, the surface of the solid phase such as e.g. the silica solid phase is not modified and is, e.g., not modified with functional groups.

According to a preferred embodiment, a solid phase comprising silicon dioxide is used. Silica based nucleic acid isolation methods are broadly used in the prior art. The solid phase comprising silica may e.g. have the form of a filter, membrane or particles. In particular preferred is the use of silica particles that can be used in form of beads and which preferably have a particle size of about 0.02 to 30 µm, more preferred 0.05 to 15 µm and most preferred of 0.1 to 10 µm. To ease the processing of the nucleic acid binding solid phase, preferably magnetic silica particles are used. The magnetic silica particles may e.g. be ferrimagnetic, ferromagnetic, paramagnetic or superparamagnetic. Suitable magnetic silica particles are for example described in WO 01/71732, WO 2004/003231 and WO 2003/004150. Other magnetic silica particles are also known from the prior art and are e.g. described in WO 98/31840, WO 98/31461, EP 1 260 595, WO 96/41811 and EP 0 343 934 and also include for example magnetic silica glass particles. Preferably, said magnetic silica particles have a silica surface to which the nucleic acid adsorbs. Said surface may be porous.

As described above, it is preferred to use magnetic particles as nucleic acid binding solid phase. The magnetic particles can be e.g. superparamagnetic, paramagnetic, ferromagnetic or ferrimagnetic. Particularly preferred is the use of magnetic silica particles as this use is widely established and very suitable for automation. The magnetic particles can be processed i.e. moved by the aid of a magnetic field, e.g. by using a permanent magnet. Here, different systems exist in the prior art that can be used in conjunction with the present invention. According to one embodiment, the magnetic particles are collected at the bottom or the side of the reaction vessel and the aqueous phase and preferably also the water-immiscible phase is removed from the reaction vessel, leaving behind the collected magnetic particles that carry the bound nucleic acids. Then, subsequently, washing and/or elution steps can be performed, as will be described in detail in the following. For this purpose, e.g. a washing and/or elution buffer can be added to the collected magnetic particles. Such systems are well known in the prior art and thus need no detailed description.

In an alternative system that is known for processing magnetic particles the magnet which is usually covered by a cover or envelope plunges into the reaction vessel to collect the magnetic particles. This embodiment is particularly preferred if the water-immiscible phase is provided on top of the food enrichment sample and remains there during step c) and during nucleic acid binding in step d). In this case, the magnet plunges through the water-immiscible phase to collect the magnetic particles that carry the bound nucleic acids. Then, the magnetic particles are transferred through the water-immiscible layer and are transferred for example into a new reaction vessel e.g. comprising a washing and/or an elution solution. As this system is well-known in the prior art, it does not need any detailed description here. It is believed that transferring the magnetic particles through the water-immiscible phase has the advantage that at least a portion of the inhibitors that might still be in contact with the nucleic acids and/or the magnetic particles is held back in the water-immiscible phase, thereby supporting the inhibitor depletion effect.

According to one embodiment, the magnetic particles are added to the reaction vessel prior to adding the food enrichment sample. This embodiment has advantages if the method according to the present invention is used in automated systems, as the risk of cross contaminations can be reduced. When adding the magnetic particles prior to adding the food enrichment sample, the addition of the magnetic particles does not pose the risk, that sample components are accidentally transferred when the magnetic particles are added.

According to one embodiment, the binding of the nucleic acids to the solid phase is performed under conditions having one or more, preferably at least two of the following characteristics:

a) binding is performed in the presence of at least one chaotropic agent,
b) binding is performed in the presence of at least one alcohol,
c) binding is performed in the presence of at least one detergent.

According to one embodiment, the binding of the nucleic acids to the solid phase is performed in step d) in the presence of at least one chaotropic agent, preferably a chaotropic salt and/or in the presence of at least one alcohol. Also a mixture of chaotropic agents can be used. Preferably, the chaotropic agent is added in form of a binding solution. The concentration of the chaotropic agent or mixture of chaotropic agents in the binding solution may lie in a range of 0.05M up to the saturation limit. Preferred concentration ranges lie, depending on the chaotropic agent used, within 0.1M to 7M, 1M to 7M, 1.5M to 6M and 2M to 4M. Suitable chaotropic agents that can be used to promote binding of the nucleic acids to the solid phase are in particular chaotropic salts and include but are not limited to guanidinium hydrochloride, guanidinium thiocyanate, guanidinium isothiocyanate, sodium thiocyanate, sodium iodide, sodium perchlorate, sodium trichloroacetate, sodium trifluoroacetate, urea and the like and in particular preferred are guanidinium hydrochloride, guanidinium thiocyanate and guanidinium isothiocyanate. As discussed above, the lysed sample may already comprise at least one chaotropic agent if such agent was added to promote the lysis in step c). In this case a chaotropic agent does not need to be added in step d) in order to promote binding of the nucleic acids to the nucleic acid binding solid phase. However, it is also within the scope of the present invention to additionally add at least one chaotropic agent in step d) e.g. in form of an aqueous binding solution if desired. Preferably, the concentration of the chaotropic agent in the binding mixture lies in a range selected from 0.05M to 4M, 0.5M to 3M, 0.75M to 2.5M and 1.0M to 1.5M.

As alcohol that can be used to promote binding, it is preferred to use short chained branched or unbranched alcohols with preferably one to 5 carbon atoms. Examples are methanol, ethanol, propanol, isopropanol and butanol. Also mixtures of alcohol can be used. The alcohol is preferably selected from isopropanol and ethanol, particularly well suitable is isopropanol. As discussed above, alcohol may already be added prior to performing the thermal lysis. In this case alcohol does not need to be added in step d) in order to promote binding of the nucleic acids to the nucleic acid binding solid phase. However, it is also within the scope of the present invention to additionally add at least one alcohol in step d) e.g. in form of an aqueous binding solution if desired. Preferably, the method according to the present invention does not involve the use of phenol and/or chloroform.

The alcohol may be comprised in the binding mixture in a concentration selected from 10% v/v to 90% v/v, 15% v/v to 70% v/v, 20% to 50% v/v and 20% v/v to 35% v/v. The concentration of the alcohol influences the binding of the nucleic acids. Higher alcohol concentrations promote binding of shorter nucleic acids. The primary target for pathogen detection is the isolation of genomic pathogen DNA. Genomic bacteria DNA has a high molecular weight. Accordingly, it can be beneficial to use lower alcohol concentrations as this reduces the binding of shorter non-target DNA such as e.g. fragmented food sample DNA.

The term "binding mixture" as used herein in particular refers to the composition wherein the binding conditions were established for binding the nucleic acids such as in particular the pathogen DNA to a nucleic acid binding solid phase. The binding mixture comprises the lysed food enrichment sample and optionally one or more reagents, such as e.g. the chaotropic agent, the alcohol and/or optionally other additives that might have been added to the lysed sample to establish, respectively improve the binding conditions. However, as described above, depending on the used protocol, it is also within the scope of the present invention that the binding conditions are already established after lysis, in particular if a lysis/binding solution is added prior to or during step c). If a nucleic acid binding solid phase is used that is mixed, e.g. dispersed in the binding mixture, as is usually the case when using particles such as magnetic particles, said nucleic acid binding solid phase also belongs to the binding mixture. If the nucleic acid binding solid phase is a column or a membrane, it does not belong to the binding mixture and accordingly, is not considered when determining the concentration(s) described above. The water-immiscible phase does not form part of the binding mixture.

Optionally, one or more detergents can be present during binding to promote binding of the nucleic acid to the solid phase. Preferably, at least one ionic and/or at least one non-ionic detergent is added. Preferably, a non-ionic detergent is added. Suitable examples are described above in conjunction with the lysis. It is referred to the respective disclosure. Said detergent can be added, e.g., together with the binding solution or can added already for lysis of the sample as is described above.

According to one embodiment, the isolation in step d) is performed using binding conditions having one or more of the following characteristics to bind the nucleic acids to the nucleic acid binding solid phase:

a) an alcohol concentration is used that is selected from the group consisting of 10% v/v to 80% v/v, 15% v/v to 60% v/v, 20% v/v to 40% v/v, 20% v/v to 35% v/v and 25% v/v to 30% v/v;
b) one or more chaotropic agents are provided in a concentration that is selected from the group consisting of 0.05M up to the saturation limit, 0.5M to 6M, 0.75M to 3M and 0.75M to 2M, and
c) optionally a detergent in a concentration selected from 0.01% to 10%, 0.1% to 7.5% and 0.5% to 5%.

The respective binding conditions are established in the binding mixture. Examples of suitable alcohols, chaotropic agents, in particular chaotropic salts and detergents are described above. It is referred to the above disclosure.

To establish respective binding conditions, a binding solution which comprises e.g. the alcohol and the chaotropic agent can be added to the lysed sample or prior to thermal lysis as lysis/binding solution. The lysis and/or lysis/binding solution may comprise a buffer. Preferably, a biological buffers such as HEPES, MES, MOPS, TRIS, BIS-TRIS Propane and others. Preferably, a Tris buffer is used.

It is also within the scope of the present invention to perform additional intermediate steps than the ones described herein. However, according to certain embodiments, no additional steps other than the ones described herein are performed.

According to one embodiment, one or more washing steps are performed in step d) in order to further purify the nucleic acids. According to one embodiment, one or more washing steps are performed while the nucleic acid is bound to the nucleic acid binding solid phase. For this purpose common washing solutions may be used. According to one embodiment, the solution used for washing comprises at least one chaotropic agent and at least one alcohol. Chaotropic salts that can be used in the washing solutions include but are not limited to guanidinium hydrochloride, guanidinium thiocyanate, guanidinium isothiocyanate and sodium iodide or other chaotropic salts. As alcohol, short chained branched or unbranched alcohols with preferably one to 5 carbon atoms can be used for washing, respectively in the washing solution. Examples are methanol, ethanol, propanol, isopropanol and butanol. Preferably, isopropanol and/or ethanol are used. Preferably, the washing solution comprises at least 20% alcohol and at least 1M chaotropic salt, preferably at least 2M chaotropic salt, more preferred at least 3M chaotropic salt, more preferred at least 4M chaotropic salt, most preferred at least 5M chaotropic salt. The washing solution may also comprise a detergent such as a non-ionic detergent.

A further suitable washing solution which can be used alternatively or optionally also in addition to the washing solutions described above comprises an alcohol but no salt. Preferably, the alcohol is comprised in a concentration of at least 50% v/v, at least 60% v/v, preferably at least 70% v/v. Preferably, the concentration lies in a range of 50% v/v to 100% v/v, more preferred 70% v/v to 100% v/v. Optionally, a drying step can be performed in order to ensure that all alcohol present in the washing solution evaporated. This avoids an alcohol carry-over into the subsequent analysis which might be sensitive to respective contaminations. After washing, optionally a water rinse can be performed.

Preferably, at least two washing steps, preferably as are described above, are performed.

According to one embodiment, the nucleic acid binding solid phase is directly subjected with the bound nucleic acid to an analysis such as e.g. an amplification reaction. This can be performed e.g. if the nucleic acid binding solid phase is provided by particles, e.g. magnetic particles. It is well known that it is e.g. possible to directly subject a nucleic acid binding solid phase with the bound nucleic acids into a PCR reaction. The nucleic acids are here at least partially eluted due to the PCR conditions. However, preferably, a separate elution step is performed in step d). Here, elution can be performed for example with classical elution solutions such as water, elution buffers, in particular biological buffers such as Tris or other suitable biological buffers and preferably elution solutions are used that do not interfere with the intended downstream application. Therefore, e.g. low salt solutions can be used for elution. The elution solution may comprise azide. Elution may also be assisted by heating.

According to a preferred embodiment, the method according to the present invention comprises the following steps:
a) providing a food enrichment culture;
b) transferring a portion of the food enrichment culture into a reaction vessel thereby providing a food enrichment sample and providing a water-immiscible phase in contact with the food enrichment sample;
c) performing a thermal treatment to promote bacteria lysis;
d) isolating nucleic acids from the lysed sample by binding the nucleic acids to magnetic particles, wherein the nucleic acid isolation comprises the following steps:
  i) establishing the binding conditions by adding a binding composition to the lysed sample thereby providing a binding mixture and binding nucleic acids to magnetic particles comprised in the binding mixture;
  ii) separating the magnetic particles with the bound nucleic acids from the remaining sample;
  iii) optionally washing the nucleic acids while bound to the magnetic particles;
  iv) optionally eluting the nucleic acids from the magnetic particles.

Details of the individual steps and preferred embodiments of each step were described above. It is referred to the above disclosure. According to one embodiment, thermal lysis is performed in the absence of additives that promote sample lysis. Here, preferably, all reagents necessary to promote the binding of the nucleic acids to the solid phase are added to the lysed sample. Preferably, in step b) the water-immiscible phase is provided on top of the food enrichment sample. More preferred, the water-immiscible phase remains on top of the sample during step c). Furthermore, it is preferred that the water-immiscible phase remains on top of the binding mixture obtained in step i) and that during separation step ii), the magnetic particles with the bound nucleic acids are transferred through the water-immiscible phase. As discussed above, transferring the magnetic particles with the bound nucleic acids through the water-immiscible phase improves the purification results. There are several possibilities to include the magnetic particles in the binding mixture. According to one embodiment, the magnetic particles are added to the reaction vessel prior to or during steps a), b) or c). As discussed above, adding the magnetic particles prior to adding the food enrichment sample to the reaction vessel may reduce the risk of cross-contaminations. However, the magnetic particles may also be added to the lysed sample in step d) e.g. in step i) prior to or after adding the binding composition.

According to a further embodiment, the method comprises the following steps:
a) providing a food enrichment culture;
b) transferring a portion of the food enrichment culture into a reaction vessel thereby providing a food enrichment sample and providing a water-immiscible phase in contact with the food enrichment sample and adding a composition comprising a chaotropic salt and optionally one or more compounds or reagents selected from the group consisting of detergents, alcohols and buffers, wherein the composition can be added before or after the water-immiscible phase was provided;
c) performing a thermal treatment to promote bacteria lysis;
d) isolating nucleic acids from the lysed sample using magnetic particles, wherein the nucleic acid isolation comprises the following steps:
  i) binding nucleic acids to magnetic particles;
  ii) separating the magnetic particles with the bound nucleic acids from the remaining sample;
  iii) optionally washing the DNA while bound to the magnetic particles;
  iv) optionally eluting the nucleic acids from the magnetic particles.

Details of the individual steps and preferred embodiments of each step were described above. It is referred to the above disclosure. According to this embodiment, thermal lysis is performed in the presence of additives that promote sample lysis such as in particular the chaotropic agent such as the chaotropic salt. Here, preferably, all reagents necessary to promote the binding of the nucleic acids to the solid phase are added to the lysed sample. In this case, it is not necessary, even though possible, to add further reagents in step d) to promote binding of the nucleic acids to the solid phase. Preferably, in step b) the water-immiscible phase is provided on top of the food enrichment sample. More preferred, the water-immiscible phase remains on top of the sample during step c). Furthermore, it is preferred that the water-immiscible phase remains on top during binding in step i) and that during separation step ii), the magnetic particles with the bound nucleic acids are transferred through the water-immiscible phase. As discussed above, transferring the magnetic particles with the bound nucleic acids through the water-immiscible phase improves the purification results. There are several possibilities to include the magnetic particles in the binding mixture. According to one embodiment, the magnetic particles are added to the reaction vessel prior to or during steps a), b) or c). As discussed above, adding the magnetic particles prior to adding the food enrichment sample to the reaction vessel may reduce the risk of cross-contaminations. However, the magnetic particles may also be added to the lysed sample in step d) i).

As discussed above, the water-immiscible phase is preferably present during the thermal lysis performed in step c) and accordingly is present during thermal lysis in both of the specifically preferred embodiments described above. Furthermore, it is preferred that it is also present during binding. A prolonged contact between the water-immiscible phase and the sample is beneficial as it is assumed that more inhibitors can be depleted into the water-immiscible phase. Furthermore, it is preferred that the magnetic particles with the bound nucleic acids are transferred through said water-immiscible phase during separation.

Contacting the food enrichment sample with the water-immiscible phase as is taught by the present invention results in a depletion of food-borne inhibitors from the food enrichment sample compared to an identical method wherein the water-immiscible phase is not provided. In particular, as is shown by the examples contacting the food enrichment sample with the water-immiscible phase results in a an increased purity and/or quality of the isolated nucleic acids, in particular genomic DNA, compared to an identical method wherein the water-immiscible phase is not provided.

This effect on the purity and/or quality can be demonstrated by performing a real-time PCR experiment, e.g. as is described in the examples.

According to one embodiment, a kit is used in the method according to the present invention comprising:
- a nucleic acid binding solid phase;
- a composition comprising a chaotropic salt and optionally one or more compounds or reagents selected from the group consisting of detergents, alcohols and buffers;
- an organic composition preferably comprising or consisting of hydrocarbons for providing the water-immiscible phase;
- optionally washing and elution solutions.

Such kits can be provided advantageously for use in automated systems. As described above, preferably magnetic particles, in particular magnetic silica particles, are used as nucleic acid binding solid phase.

As nucleic acids, DNA and RNA can be isolated. The method according to the present invention is in particular suitable for isolating DNA, in particular genomic DNA from food samples. RNA can get degraded during the thermal lysis step, in particular if a chaotropic agent is added for thermal lysis. If a pathogen such as pathogen bacteria is comprised in the food enrichment culture, the DNA, in particular the genomic bacteria DNA can be isolated with good efficiency and purity with the method according to the present invention.

According to one embodiment, the method comprises a further step e) wherein the isolated nucleic acid is analysed. In particular, such analysis may comprise the detection of the presence or absence of one or more pathogen nucleic acids in the isolated nucleic acids. The method according to the invention is useful for the detection of any food pathogen, in particular microbial pathogens. The method according to the present invention in particular allows the isolation of bacteria DNA, in particular from gram-positive or gram-negative bacteria. According to one embodiment, the method is used for detection of a food pathogen selected from the group comprising *Salmonella, Listeria, Legionella, E. coli, Shigella, Campylobacter, Vibrio, Cronobacter, Staphylococcus, Yersinia* and emerging pathogens.

The analysis of the isolated nucleic acids for the presence of pathogen nucleic acids such as in particular pathogen DNA can be performed using any nucleic acid analysis method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof. Respective technologies are well-known to the skilled person and thus, do not need further description here. In particular preferred are methods that are based on nucleic acid amplification. Pathogens in foods are often found at lower levels than in samples taken from people that are ill. Thus, the nucleic acid extraction must not only be quick to serve the demands of the food industry but also very efficient. In particular, the DNA must be provided in a sufficient purity and quality to allow the detection of any comprised pathogen with the intended analytical methods, in particular an amplification reaction which also allows to detect very small amounts of pathogen nucleic acid such as bacteria DNA in the isolated DNA. Knowing the sequence of a pathogen's nucleic acid enables the scientist to construct primers and/or probes that allow to detect said pathogen.

Furthermore, the present invention pertains to a method for detecting the presence or absence of at least one pathogen nucleic acid in a food sample, comprising performing the method according to the present invention and detecting the presence or absence of at least one pathogen nucleic acid in the isolated nucleic acids. Preferably, the target pathogen nucleic acid is detected using an amplification method, preferably by polymerase chain reaction. Typical pathogens and analysis methods are described above, it is referred to the respective disclosure. As described above, the method is in particular suitable for detecting gram-positive and gram-negative bacteria. Furthermore, also with respect to the nucleic acid isolation method it is referred to the above detailed disclosure.

According to a third aspect, the present invention pertains to the use of a water-immiscible composition for removing inhibitors from a food enrichment sample. The water-immiscible composition is contacted with the food enrichment sample, thereby forming a water-immiscible phase that is in contact with the food enrichment sample. The food enrichment sample preferably is obtained from a food enrichment culture. Preferably, the food enrichment sample is an aliquot of an unprocessed food enrichment culture. The present invention shows that a water-immiscible composition such as mineral oil can be used as an efficient purification reagent for the depletion of organic, liposoluble and/or lipophilic inhibitors from unprocessed food enrichment culture samples. In particular, the water-immiscible composition such as mineral oil can be used as an efficient purification reagent for the depletion of unpolar, organic, liposoluble and/or lipophilic food-borne or pathogen-borne inhibitors of a molecular biological detection method, such as an enzymatic reaction, e.g. an amplification reaction, in particular a PCR reaction. As discussed above, to efficiently remove such inhibitors signifies a major challenge in the reliable detection of PCR-ready bacterial DNA from food enrichment cultures. As is shown herein, a water-immiscible phase that is provided e.g. on top of the food enrichment sample interacts directly with the food enrichment sample thereby optimizing the subsequent DNA purification result due to a removal of inhibitory components comprised in the food enrichment sample. It is preferred to directly contact the food enrichment sample (that can be obtained e.g. as aliquot from the food enrichment culture) with the water-immiscible composition to form a water-immiscible phase prior to isolating the nucleic acids from the food enrichment sample. Thereby, a maximal interaction of the aqueous food enrichment sample with the lipophilic, water-immiscible phase is ensured and this interaction occurs at the beginning of the nucleic acid isolation with the chemically unaltered sample material, containing unlysed and viable bacteria. By bringing the food enrichment sample and the water-immiscible composition into direct contact before the actual DNA extraction procedure starts, at least a portion of the organic and/or liposoluble inhibitors comprised in the food enrichment sample (wherein respective inhibitors are usually comprised in a high concentration) is expected to cross the phase interface into the water-immiscible phase due to an enhanced solubility in the organic phase and are thereby depleted from the aqueous sample.

Preferably, in the use according to the third aspect of present invention the food enrichment sample that has been contacted with a water-immiscible composition to provide a water-immiscible phase subjected to a lysis step, wherein preferably a thermal treatment as described above in conjunction with the method according to the first aspect of the present invention is performed, and subsequently nucleic acids are isolated from the lysed sample, preferably by performing an isolation step as is described in conjunction with the method according to the first aspect of the present invention. Preferably, the water-immiscible phase remains in contact with the aqueous phase during lysis, preferably on top thereof, as thereby also inhibitors that are released during lysis, e.g. from lysed pathogens, can be at least partially removed from the aqueous phase. As is shown in the examples, the use of a water-immiscible composition as provided by the present invention is advantageous for the isolation of nucleic acids such as DNA from food-borne pathogens, in particular bacteria, that are comprised in the food enrichment sample. Owing to the application of the water-immiscible composition enhanced depletion of food- and bacteria-derived inhibitors occurs and results in isolated nucleic acids such as genomic bacteria DNA of a noticeably higher quality and purity. The examples show that nucleic acids such as DNA that are isolated from a respectively treated food enrichment sample provide better results in the subsequent detection steps, in particular when using detection methods that involve an amplification step such as a PCR reaction. Details with respect to the water-immiscible composition and the subsequent preparation steps such as thermal lysis and nucleic acid isolation were described in detail above in conjunction with the method according to the first aspect of the present invention. It is referred to the respective disclosure which also applies here.

The term "solution" as used herein, e.g. as lysis solution in particular refers to a liquid composition, preferably an aqueous composition. It may be a homogenous mixture of only one phase but it is also within the scope of the present invention that a solution that is used according to the present invention comprises solid components such as e.g. precipitates.

According to one embodiment, subject matter described herein as comprising certain steps in the case of methods or as comprising certain ingredients in the case of compositions, solutions and/or buffers refers to subject matter consisting of the respective steps or ingredients.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

The method according to the present invention is now described by way of non-limiting examples.

EXAMPLES

1. Materials and Methods

The following materials were used in the examples:
Binding Buffer
  Comprises a chaotropic agent, a non-ionic detergent and isopropanol (Buffer QSB1, QIAGEN)
Washing Buffer 1
  Comprises a chaotropic agent, a non-ionic detergent and isopropanol. It has an acidic pH value (Buffer QSW1, QIAGEN)
Washing Buffer 2
  80% ethanol
Elution Buffer
  TE forensic (ATE) (QIAGEN)
TopElute
  Mineral oil (Sigma Aldrich (M5904))
Nucleic Acid Binding Solid Phase
  Magnetic silica beads (MagAttract Beads)

The efficiency of the method according to the present invention is demonstrated in examples 1 and 2 based on two protocol variants (1) and (2), which are described in further detail below in the individual examples. Both protocols start from unprocessed food enrichment culture samples. A food enrichment culture is prepared with 25 g of a food sample and 225 ml of a bacteria specific enrichment medium. Both components are mixed in a lab pedal blender and incubated at raised temperatures for a defined time. As sample, an aliquot of the unprocessed enrichment culture is used for DNA extraction.

The automated extraction and purification of bacterial DNA from food enrichment cultures is based on two extraction protocols (1) and (2) designed for use with the QIAsymphony Sample Preparation (SP) instrument (QIAGEN). DNA extraction occurs using magnetic, silica-coated beads, to which released DNA molecules adsorb under defined binding conditions. As unprocessed food enrichment culture samples serve as the default starting material both automated extraction protocols initially process viable and intact bacteria.

After transfer of 400 µA of the sample material to the QIAsymphony Sample Prep Cartridge, a 170 µl layer of TopElute Fluid is added on top of the aqueous sample material phase as a first step of both automation protocols. Direct combination of these initial process steps ensures maximal interaction of the aqueous sample solution with the lipophilic, water insoluble TopElute phase. As this interaction takes placed at the beginning of both extraction protocols the TopElute interacts with the chemically unaltered sample material, containing unlysed and viable bacteria. As discussed above, food enrichment culture samples are known to contain high concentrations of organic and/or liposoluble inhibitors. By bringing the enrichment culture sample and the TopElute into direct contact before the actual DNA extraction procedure starts, part of the lipophilic inhibitors comprised in the sample is expected to cross the phase interface into the organic phase due to an enhanced solubility. This small scale phase extraction between the aqueous sample solution and the TopElute Fluid most likely leads to an initial depletion of food derived inhibitors, allowing for an important cleaning effect before the actual bacteria lysis takes place, thereby improving the DNA extraction and the subsequent DNA detection.

Bacteria lysis itself subsequently occurs via a thermal treatment at 89° C. for 5 min without shaking. At this stage the two extraction protocols (1) and (2) start to diverge. In Protocol (1) the thermal lysis starts directly after dispension of the TopElute, thus effecting a chemically unaided, mild lysis which is in particular suitable for gram-negative bacteria such as *Salmonella*. In Protocol (2) addition of the chaotropic binding buffer occurs prior to the heat treatment. The presence of the chaotropic buffer during the thermal treatment leads to tightened lysis conditions, which further enhance lysis efficiency and which make Protocol (2) particularly suitable for the lysis of gram-negative and gram-positive bacteria such as *Salmonella* and *Listeria*.

In both protocols (1) and (2) bacteria lysis takes place in a preset two-component system in which the aqueous phase containing the sample material is already provided with a TopElute overlay. While in the Protocol (1) the lysis is entirely based on the heat treatment, the lysis in Protocol (2) is chemically aided by the presence of the chaotropic binding buffer. In both protocols the TopElute overlay is expected to extract and deplete food-derived inhibitors as well as additional bacteria-derived inhibitors liberated during the lysis procedure. In both Protocols (1) and (2) according to the invention the magnetic, silica coated beads are added into the heated reaction solution after the thermal lysis procedure. In Protocol (1) addition of the magnetic beads is then followed by the addition of binding buffer. Both Protocols (1) and (2) according to the invention then proceed via a two-step washing procedure for which the beads together with the bound DNA are transferred from the initial reaction solution to a well containing the first wash buffer.

Owing to the application of the TopElute Fluid an efficient depletion of food- and bacteria-derived inhibitors is achieved, whereby the Protocols (1) and (2) according to the invention provide bacterial DNA of a noticeably higher quality and purity.

This remarkable effect that is achieved by the method according to the present invention is subsequently demonstrated by comparing the Protocols (1) and (2) to identical protocols, wherein, however, the TopElute overlay step was omitted. The data verifying the TopElute-mediated increase in DNA quality and thus increased reliability of the DNA detection via real-time PCR is demonstrated by the subsequent Examples 1 and 2.

2. Example 1

The first set of data was obtained with Protocol (1), in which the bacteria lysis is chemically unaided and based entirely on a thermal treatment at 89° C. To directly assess the influence of the TopElute treatment an analogous protocol, featuring the same process steps but lacking the TopElute overlay, was programmed and both protocols were tested in parallel.

To test the inhibitor removal capacity of the TopElute pre-purification step, enrichment cultures of two strongly inhibitory matrices were prepared. For a first culture smoked salmon and for a second culture ground beef was mixed with the enrichment medium Buffered Peptone Water and inoculated with ~20 cfu of *Salmonella enterica*. Although the LFGB § 64 recommends a 1:10 ratio of food to medium (25 g of food and 225 ml of enrichment medium) a 1:6 ratio of food to medium (25 g of food and 125 ml of enrichment medium) was chosen to test the protocols. This ratio results in a higher background load of food matrix per ml but represents a more realistic scenario than the 1:10 ratio, as it is frequently applied in time- and cost-sensitive routine food service labs. Moreover, an increased matrix ratio allows a more significant evaluation of the inhibitor removal capacity of the TopElute Fluid.

For a better overview of the protocol steps the table provided below shows Protocol (1) as well as the comparative example.

| | Protocol (1) (without chaotropic binding buffer in the thermal lysis) | |
|---|---|---|
| Step | Description | Specification |
| 1 | Transfer of the unprocessed food enrichment sample from the primary tube into the reaction vessel | 400 µl |
| 2 | Oil overlay of the sample in the reaction vessel N.B: This oil overlay step was omitted in the comparative example) | 170 µl |
| 3 | Heating of the reaction solution to lyse the bacteria | 89° C., 5 min |
| 4 | Addition of the MagAttract beads | 60 µl |
| 5 | Addition of the binding buffer to reaction solution | 480 µl |
| 6 | Transfer of the beads including the bound DNA in a new reaction vessel comprising the washing buffer 1 | 950 µl |
| 7 | Transfer of the beads including the bound DNA in a new reaction vessel comprising washing buffer 2 | 800 µl |
| 8 | Implementation of a water-rinse | 480 µl |
| 9 | Elution of the purified DNA | 200 µl |

Figure 1B:
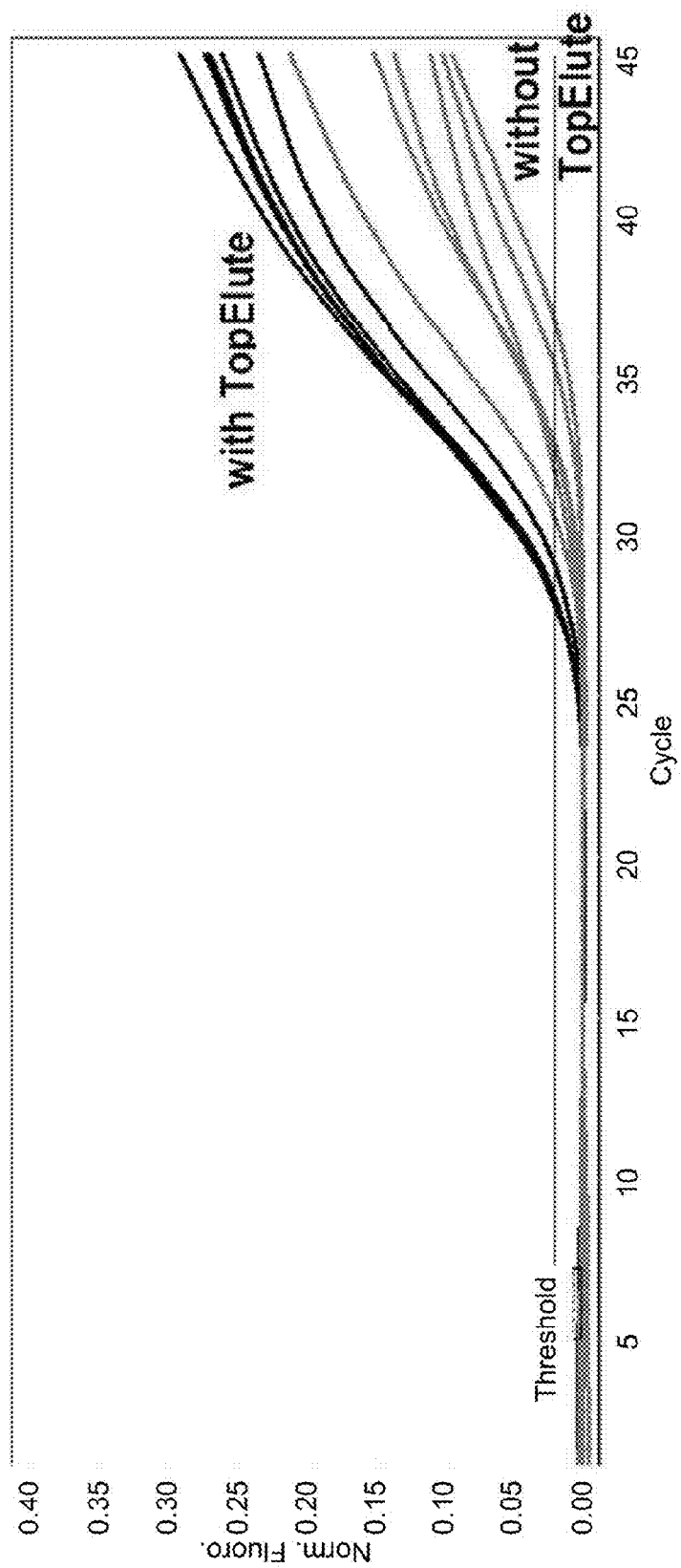

After running samples of both enrichment cultures (smoked salmon and ground beef) with the two tested protocols (Protocol (1) according to the invention and comparative example wherein the TopElute overlay was omitted in the otherwise unaltered protocol) the eluted DNA was analyzed via real-time PCR, applying the mericon *Salmonella* spp Detection Assay. The results for smoked salmon are shown in FIG. 1A and for ground beef in FIG. 1B. In each figure the amplification curves for the *Salmonella* DNA obtained with and without the application of TopElute are compared. The progression of the curves in both graphs clearly shows a strong increase of the DNA amplification efficiency and the overall quality of detection when applying the TopElute step to deplete inhibitors. Owing to the additional cleaning effect of the TopElute the detection sensitivity was increased by ~6 Cts for smoked salmon and ~5 Cts for ground beef.

Figure 2:
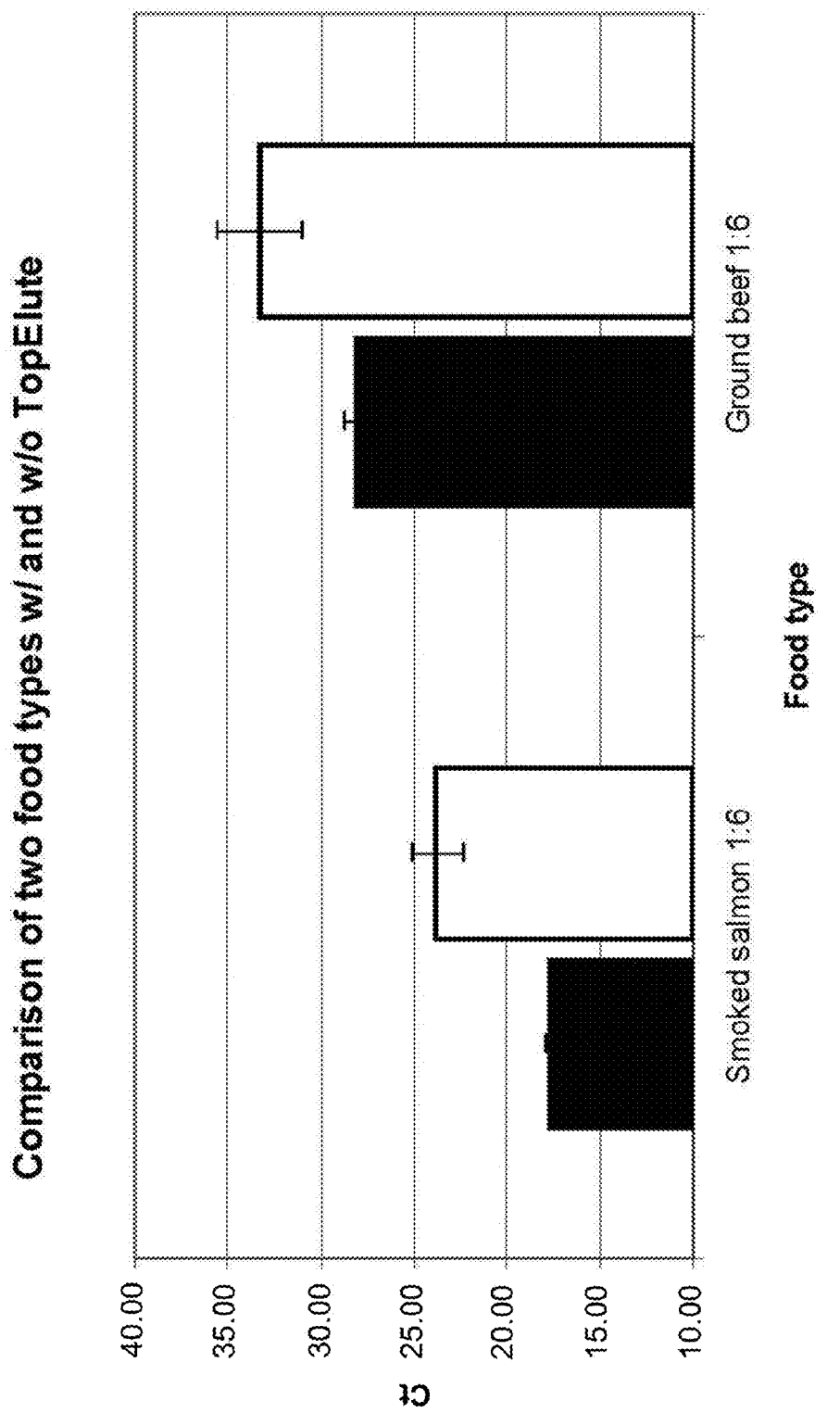
FIG. 2: Summary of the smoked salmon and ground beef data illustrated in FIG. 1. Shown here are the mean Ct values including standard deviations of the measured 6 sample replicates. Ct differences between the mean Cts of both protocols for the respective food types are indicated above the column plots. As can be seen, Protocol (1) that according to the teaching of the present invention overlays the food enrichment sample with a water-immiscible phase provides significantly better, i.e. lower Ct values.

Mean Ct values of the curve sets for both food types and the differences between the separate protocols are summarized in FIG. 2. Next to lower Ct values observed the case of the TopElute protocol, the data also shows that the high degree of Ct scattering, observed in the protocol without TopElute, could be strongly diminished. This is an important advantage as the reliability is increased. Furthermore, there is a noticeable improvement in the values and scattering of the end fluorescences of the TopElute curve set. Improvements on Ct, overall data scattering and end fluorescence are classical indicators for a significant depletion of inhibitors interfering with the PCR analysis. These results confirm that a TopElute mediated inhibitor depletion during the DNA isolation procedure results in a clear improvement of the quality of the DNA and reliability of the subsequent real-time PCR analysis.

3. Example 2

The second set of data was obtained with Protocol (2) in which the bacteria lysis is chemically aided by the presence of the chaotropic binding buffer during the heat treatment at 89° C. Again, to directly assess the influence of the TopElute treatment under these modified lysis conditions an analogous protocol, featuring the same process steps but lacking the TopElute overlay, was programmed on the QIAsymphony and both protocols were tested in parallel.

For a better overview of the protocol steps the table provided below shows Protocol (1) as well as the comparative example.

| Protocol 2 (with chaotropic binding buffer in the thermal lysis) | | |
|---|---|---|
| Step | Description | Specification |
| 1 | Transfer of the unprocessed food enrichment sample from the primary tube into the reaction vessel | 400 µl |
| 2 | Oil overlay of the sample in the reaction vessel N.B: This oil overlay step was omitted in the comparative example) | 170 µl |
| 3 | Addition of the binding buffer to reaction solution | 480 µl |
| 4 | Heating of the reaction solution to lyse the bacteria | 89° C., 5 min |
| 5 | Addition of MagAttract beads to the reaction solution | 60 µl |
| 6 | Transfer of the beads including the bound DNA in a new reaction vessel comprising the washing buffer 1 | 950 µl |
| 7 | Transfer of the beads including the bound DNA in a new reaction vessel comprising washing buffer 2 | 800 µl |
| 8 | Implementation of a water-rinse | 480 µl |
| 9 | Elution of the purified DNA | 200 µl |

The test for the inhibitor removal capacity of the TopElute pre-purification step was carried out with a classical *Salmonella* associated and strongly inhibitory chocolate matrix. An enrichment culture of chocolate was prepared with the enrichment medium Buffered Peptone Water and ~20 cfu of *Salmonella enterica*. As chocolate is already one of the most demanding food types for pathogen detection this time a 1:10 food to medium ratio (25 g of food and 225 ml of enrichment medium) was tested with both protocols (Protocol (2) according to the invention and comparative example wherein the TopElute overlay step was omitted).

Figure 3:
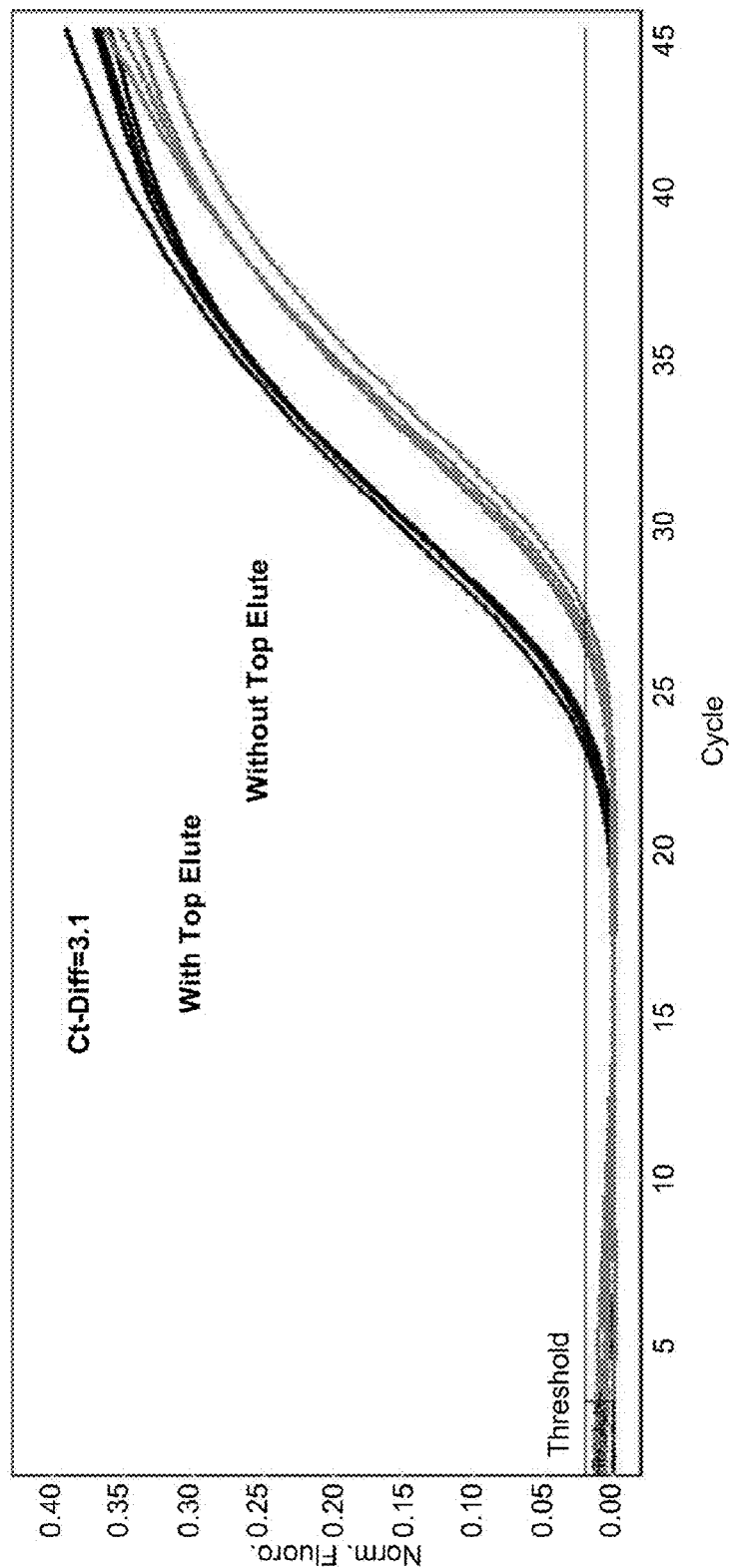
FIG. 3: Chocolate was inoculated with ~20 cfu *salmonella* and incubated in Buffered peptone Water for 18 h at 37° C. Samples of the enrichment culture were directly processed according to Protocol (2) (black), applying TopElute, and the analogous protocol lacking TopElute (grey). Comparison of both protocol performances shows an almost tenfold better performance of the TopElute applying Protocol (2) according to the present invention over the comparative example not applying a water-immiscible phase on the food enrichment sample.

After running samples of the chocolate enrichment culture with the two test protocols the eluted DNA was also analyzed via real-time PCR, applying the mericon *Salmonella* spp Detection Assay. The results are shown in FIG. 3. These results further confirm the overall improvement in the detection quality and sensitivity that was already observed with Protocol (1). Most noticeable here is the shift of the Cts to lower values as a major effect signifying a strong reduction on the inhibitor background of the eluted DNA solution. The Ct difference of 3.1 shows that almost a tenfold higher DNA concentration could be detected when TopElute was applied as an additional inhibitor removal reagent in Protocol (2) compared to the analogous protocol wherein the TopElute overlay step was omitted.

In summary the experimental data presented in the present application shows that the presence of a water immiscible, oil-based phase during the thermal lysis of viable bacteria in food enrichment culture matrices leads to a strong depletion of food-derived PCR inhibitors. This step is considered to be an important pre-cleaning procedure of the aqueous, DNA containing phase, supporting and intensifying the default DNA purification steps. The eluted DNA solution therefore contains less inhibitors which ultimately leads to a higher quality and reliability of detection in the downstream real-time PCR analysis.

The invention claimed is:

1. A method for isolating nucleic acids from a food sample comprising the following steps:
   a) obtaining a food enrichment culture;
   b) transferring a portion of the food enrichment culture into a reaction vessel thereby providing a food enrichment sample and providing a water-immiscible phase in contact with the food enrichment sample;
   c) lysing the food enrichment sample that has been contacted with the water-immiscible phase to provide a lysed sample; and
   d) isolating nucleic acids from the lysed sample.

2. The method according to claim 1, wherein the water-immiscible phase has one or more of the following characteristics:
   a. it is an organic phase which forms a closed layer on the food enrichment sample;
   b. it comprises or consist of hydrocarbons;
   c. it comprises or consists of saturated hydrocarbons;
   d. it comprises or consists of branched or unbranched, substituted or non-substituted, acyclic or cyclic hydrocarbons with 5, 6, 7, 8, 9, 10, 11, 12, 13, 14, 15, 16, 17, 18, 19 or 20 carbon atoms;
   e. it comprises or consists of mineral oil;
   f. it is provided by contacting the food enrichment sample with a water-immiscible composition having one or more of the aforementioned characteristics a. to e.; and/or
   g. it is provided on top of the food enrichment sample.

3. The method according to claim 1, wherein in step c) a thermal treatment is performed to achieve or assist lysis.

4. The method according to claim 3, wherein prior to performing the thermal treatment a chaotropic agent is added to the food enrichment sample and optionally one or more compounds or reagents selected from the group consisting of detergents, alcohols and buffers.

5. The method according to claim 1, wherein step d) comprises binding the nucleic acids to a nucleic acid binding solid phase.

6. The method according to claim 5, wherein magnetic particles are used as nucleic acid binding solid phase.

7. The method according to claim 1, wherein the water-immiscible phase is provided on top of the sample during lysis step c).

8. The method according to claim 7, wherein magnetic particles are used as nucleic acid binding solid phase for binding the nucleic acids in step d) and wherein the magnetic particles to which the nucleic acids were bound are transferred through the water-immiscible phase during nucleic acid isolation step d) and optionally washing the isolated nucleic acids in at least one washing step.

9. The method according to claim 1, wherein step d) comprises binding the nucleic acids to the nucleic acid binding solid phase in the presence of a chaotropic salt and optionally one or more compounds or reagents selected from the group consisting of detergents, alcohols and buffers.

10. The method according to claim 1, having one or more of the following characteristics:
   a. the food enrichment culture of step a) and/or b) is an unprocessed food enrichment culture;
   b. the food enrichment culture of step a) is an un-selective food enrichment culture;
   c. the water-immiscible phase is in contact with the food enrichment sample during step c) and optionally at least partially during step d);
   d. the water-immiscible phase forms a closed layer on the food enrichment sample;
   e. magnetic particles are used as nucleic acid binding solid phase for isolating nucleic acids in step d), wherein the magnetic particles are added to the food enrichment sample prior to, during or after step c);
f. magnetic particles are used as nucleic acid binding solid phase and are added to the reaction vessel prior to adding the food enrichment sample;
g. the lysis of the food enrichment sample does not involve the use of a proteolytic enzyme;
h. providing the water-immiscible phase in contact with the food enrichment sample results in a depletion of food-borne and/or pathogen-borne inhibitors from the food enrichment sample compared to an identical method wherein the water-immiscible phase is not provided in contact with the food enrichment sample;
i. providing the water-immiscible phase in contact with the food enrichment sample results in an improved purity and/or quality of the isolated nucleic acids compared to an identical method wherein the water-immiscible phase is not provided in contact with the food enrichment sample;
j. the nucleic acid to be isolated is or comprises pathogen DNA;
k. lysis step c) results in a lysis of pathogens if comprised in the food enrichment sample;
l. the food enrichment sample comprises or is suspected of comprising at least one food pathogen, which is a microbial pathogen selected from the group of gram-positive bacteria, gram-negative bacteria, *Salmonella, Listeria, Legionella, E. coli, Shigella, Campylobacter, Vibrio, Cronobacter, Staphylococcus, Yersinia* and emerging pathogens; and/or
m. the food enrichment culture is obtained by mixing a defined amount of a food sample to be tested for the presence or absence of a target food pathogen with a defined volume of an enrichment medium and incubation under conditions that allow to grow and enrich the target pathogen above an analytically detectable level.

11. The method according to claim 1, comprising the following steps:
a) contacting the food sample with a culture medium and incubation to provide a food enrichment culture;
b) transferring a portion of the food enrichment culture into a reaction vessel thereby providing a food enrichment sample and providing a water-immiscible phase in contact with the food enrichment sample;
c) performing a thermal treatment of the food enrichment sample that has been contacted with the water-immiscible phase to promote bacterial lysis; and
d) isolating nucleic acids from the lysed sample using magnetic particles, wherein the nucleic acid isolation comprises the following steps:
i) establishing binding conditions by adding a binding composition to the lysed sample thereby providing a binding mixture and binding nucleic acids to magnetic particles comprised in the binding mixture;
ii) separating the magnetic particles with the bound nucleic acids from the remaining sample;
iii) optionally washing the nucleic acids while bound to the magnetic particles;
iv) optionally eluting the nucleic acids from the magnetic particles;
or
a) contacting the food sample with a culture medium and incubation to provide a food enrichment culture;
b) transferring a portion of the food enrichment culture into a reaction vessel thereby providing a food enrichment sample, providing a water-immiscible phase in contact with the food enrichment sample and adding a composition comprising a chaotropic salt and optionally one or more compounds or reagents selected from the group consisting of detergents, alcohols and buffers, wherein the composition can be added before or after the water-immiscible phase was provided;
c) performing a thermal treatment of the food enrichment sample that has been contacted with the water-immiscible phase to promote bacterial lysis; and
d) isolating nucleic acids from the lysed sample using magnetic particles, wherein the nucleic acid isolation comprises the following steps:
i) binding nucleic acids to the magnetic particles;
ii) separating the magnetic particles with the bound nucleic acids from the remaining sample;
iii) optionally washing the nucleic acids while bound to the magnetic particles;
iv) optionally eluting the nucleic acids from the magnetic particles.

12. The method according to claim 11, wherein in step b) the water-immiscible phase is provided on top of the food enrichment sample and remains on top thereof during step c) and during binding in step d) i) and wherein in the course of separation step ii), the magnetic particles with the bound nucleic acids are transferred through the water-immiscible phase.

13. The method according to claim 1, wherein a kit is used comprising:
a nucleic acid binding solid phase;
a composition comprising a chaotropic salt and optionally one or more compounds or reagents selected from the group consisting of detergents, alcohols and buffers;
an organic composition comprising or consisting of hydrocarbons for providing the water-immiscible phase;
optionally washing and elution solutions.

14. The method according to claim 1, comprising:
e) analyzing the isolated nucleic acids.

15. The method according to claim 3, wherein in step c) a thermal treatment is performed to lyse the food enrichment sample and to lyse the pathogens comprised therein, wherein said thermal treatment comprises heating the food enrichment sample that is overlayed with the water-immiscible phase for 2 to 20 minutes at least at 80° C.

16. The method according to claim 4, wherein the chaotropic agent is a chaotropic salt and is contained in a lysis solution.

17. The method according to claim 16, wherein the lysis solution comprises at least one chaotropic salt and at least one detergent.

18. The method according to claim 17, wherein the lysis solution additionally comprises at least one alcohol and allows for the nucleic acids released from the food sample to bind to a nucleic acid binding solid phase.

19. The method according to claim 1, wherein the method is performed using an automated system and wherein unprocessed food enrichment culture samples are directly loaded onto a robotic instrument of the automated system.

20. The method of claim 1 which is for determining the presence or absence of a pathogen in a food sample, wherein the determination encompasses the detection of pathogen specific DNA in the isolated nucleic acids.

21. The method according to claim 20, wherein the pathogen is a microbial pathogen selected from the group of gram-positive bacteria, gram-negative bacteria, *Salmonella, Listeria, Legionella, E. coli, Shigella, Campylobacter, Vibrio, Cronobacter, Staphylococcus, Yersinia* and emerging pathogens.

22. The method according to claim 6, wherein the magnetic particles are magnetic silica particles.

23. The method according to claim 14, wherein step e) comprises detecting the presence or absence of one or more pathogen nucleic acids in the isolated nucleic acids.

* * * * *